(12) United States Patent
Smith

(10) Patent No.: US 8,240,636 B2
(45) Date of Patent: Aug. 14, 2012

(54) VALVE SYSTEM

(75) Inventor: Mark Forrest Smith, Longmont, CO (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 787 days.

(21) Appl. No.: 12/351,969

(22) Filed: Jan. 12, 2009

(65) Prior Publication Data
US 2010/0179464 A1    Jul. 15, 2010

(51) Int. Cl.
*F16K 31/02* (2006.01)

(52) U.S. Cl. ......... 251/129.19; 251/129.17; 251/129.02; 251/65; 137/554

(58) Field of Classification Search ............... 251/65, 251/129.02, 129.15, 129.17, 129.19; 137/553, 137/554
See application file for complete search history.

(56) References Cited

U.S. PATENT DOCUMENTS

| | | |
|---|---|---|
| 2,328,381 A | 8/1943 | Jaffe |
| 4,071,444 A | 1/1978 | Ash et al. |
| 4,348,283 A | 9/1982 | Ash |
| 4,368,737 A | 1/1983 | Ash |
| 4,387,777 A | 6/1983 | Ash |
| 4,402,694 A | 9/1983 | Ash et al. |
| 4,403,765 A * | 9/1983 | Fisher ............... 251/65 |
| 4,403,984 A | 9/1983 | Ash et al. |
| 4,413,988 A | 11/1983 | Handt et al. |
| 4,469,593 A | 9/1984 | Ishihara et al. |
| 4,498,902 A | 2/1985 | Ash et al. |
| 4,559,039 A | 12/1985 | Ash et al. |
| 4,581,141 A | 4/1986 | Ash |
| 4,661,246 A | 4/1987 | Ash |
| 4,777,953 A | 10/1988 | Ash et al. |
| 4,854,322 A | 8/1989 | Ash et al. |
| 4,914,819 A | 4/1990 | Ash |
| 4,995,268 A | 2/1991 | Ash et al. |
| 4,997,570 A | 3/1991 | Polaschegg |
| 5,002,054 A | 3/1991 | Ash et al. |
| 5,032,261 A | 7/1991 | Pyper |
| 5,100,554 A | 3/1992 | Polaschegg |
| 5,114,580 A | 5/1992 | Ahmad et al. |
| 5,147,613 A | 9/1992 | Heilmann et al. |
| 5,198,335 A | 3/1993 | Sekikawa et al. |
| 5,211,643 A | 5/1993 | Reinhardt et al. |
| 5,228,308 A * | 7/1993 | Day et al. ............ 62/198 |
| 5,230,341 A | 7/1993 | Polaschegg |
| 5,277,820 A | 1/1994 | Ash |
| 5,295,505 A | 3/1994 | Polaschegg et al. |
| 5,304,349 A | 4/1994 | Polaschegg |
| 5,308,315 A | 5/1994 | Khuri et al. |
| 5,322,258 A | 6/1994 | Bosch et al. |
| 5,322,519 A | 6/1994 | Ash |
| 5,385,005 A | 1/1995 | Ash |

(Continued)

*Primary Examiner* — John Fristoe, Jr.
*Assistant Examiner* — Time Aigbe
(74) *Attorney, Agent, or Firm* — Novel IP

(57) ABSTRACT

The present invention is directed to a valve that has an orifice closing member adjacent to an orifice through which fluid can flow, a displacement member having a first portion and a second portion, where the first portion is adjacent to the orifice closing member when the valve is in an open position, a first magnet and a second magnet where the first and second magnets are sufficiently proximate to the displacement member to exert a magnetic force on the displacement member, and an actuator for generating a magnetic field to move the displacement member toward the first magnet, cause the first portion to press against the orifice closing member, and cause the orifice closing member to close the orifice.

9 Claims, 6 Drawing Sheets

U.S. PATENT DOCUMENTS

| | | |
|---|---|---|
| D355,816 S | 2/1995 | Ash |
| 5,405,315 A | 4/1995 | Khuri et al. |
| 5,445,630 A | 8/1995 | Richmond |
| 5,476,444 A | 12/1995 | Keeling et al. |
| D370,531 S | 6/1996 | Ash et al. |
| 5,536,412 A | 7/1996 | Ash |
| 5,540,265 A | 7/1996 | Polaschegg et al. |
| 5,577,891 A | 11/1996 | Loughnane et al. |
| 5,580,460 A | 12/1996 | Polaschegg |
| 5,614,677 A | 3/1997 | Wamsiedler et al. |
| 5,616,305 A | 4/1997 | Mathieu |
| 5,624,551 A | 4/1997 | Baumann et al. |
| 5,632,897 A | 5/1997 | Mathieu |
| 5,698,083 A | 12/1997 | Glass |
| 5,711,883 A | 1/1998 | Folden et al. |
| 5,713,850 A | 2/1998 | Heilmann et al. |
| 5,725,773 A | 3/1998 | Polaschegg |
| 5,794,669 A | 8/1998 | Polaschegg et al. |
| 5,858,186 A | 1/1999 | Glass |
| 5,906,978 A | 5/1999 | Ash |
| 5,919,369 A | 7/1999 | Ash |
| 5,947,953 A | 9/1999 | Ash et al. |
| 6,042,561 A | 3/2000 | Ash et al. |
| 6,156,007 A | 12/2000 | Ash |
| 6,190,349 B1 | 2/2001 | Ash et al. |
| 6,217,540 B1 | 4/2001 | Yazawa et al. |
| 6,254,567 B1 | 7/2001 | Treu et al. |
| 6,264,680 B1 | 7/2001 | Ash |
| 6,287,516 B1 | 9/2001 | Matson et al. |
| 6,303,036 B1 | 10/2001 | Collins et al. |
| 6,332,985 B1 | 12/2001 | Sherman et al. |
| 6,348,162 B1 | 2/2002 | Ash |
| 6,409,699 B1 | 6/2002 | Ash |
| 6,471,872 B2 | 10/2002 | Kitaevich et al. |
| 6,497,675 B1 | 12/2002 | Davankov |
| 6,517,045 B1 | 2/2003 | Northedge |
| 6,551,513 B2 | 4/2003 | Nikaido et al. |
| 6,554,789 B1 | 4/2003 | Brugger et al. |
| 6,572,576 B2 | 6/2003 | Brugger et al. |
| 6,572,641 B2 | 6/2003 | Brugger et al. |
| 6,579,253 B1 | 6/2003 | Burbank et al. |
| 6,579,460 B1 | 6/2003 | Willis et al. |
| 6,582,385 B2 | 6/2003 | Burbank et al. |
| 6,589,482 B1 | 7/2003 | Burbank et al. |
| 6,595,943 B1 | 7/2003 | Burbank |
| 6,623,470 B2 | 9/2003 | Munis et al. |
| 6,627,164 B1 | 9/2003 | Wong |
| 6,638,477 B1 | 10/2003 | Treu et al. |
| 6,638,478 B1 | 10/2003 | Treu et al. |
| 6,649,063 B2 | 11/2003 | Brugger et al. |
| 6,673,314 B1 | 1/2004 | Burbank et al. |
| 6,702,561 B2 | 3/2004 | Stillig et al. |
| 6,730,266 B2 | 5/2004 | Matson et al. |
| 6,743,193 B2 | 6/2004 | Brugger et al. |
| 6,818,196 B2 | 11/2004 | Wong |
| 6,830,553 B1 | 12/2004 | Burbank et al. |
| 6,836,201 B1 | 12/2004 | Devenyi et al. |
| 6,841,172 B1 | 1/2005 | Ash |
| 6,852,090 B2 | 2/2005 | Burbank et al. |
| 6,872,346 B2 | 3/2005 | Stillig |
| 6,878,283 B2 | 4/2005 | Thompson |
| 6,955,655 B2 | 10/2005 | Burbank et al. |
| 6,958,049 B1 | 10/2005 | Ash |
| 6,960,179 B2 | 11/2005 | Gura |
| 6,960,328 B2 | 11/2005 | Bortun et al. |
| 6,979,309 B2 | 12/2005 | Burbank et al. |
| 7,004,924 B1 | 2/2006 | Brugger et al. |
| 7,033,498 B2 | 4/2006 | Wong |
| 7,040,142 B2 | 5/2006 | Burbank |
| 7,087,033 B2 | 8/2006 | Brugger et al. |
| 7,101,519 B2 | 9/2006 | Wong |
| 7,112,273 B2 | 9/2006 | Weigel et al. |
| 7,115,095 B2 | 10/2006 | Eigler et al. |
| 7,135,156 B2 | 11/2006 | Hai et al. |
| 7,144,386 B2 | 12/2006 | Korkor et al. |
| 7,147,613 B2 | 12/2006 | Burbank et al. |
| 7,169,303 B2 | 1/2007 | Sullivan et al. |
| 7,175,809 B2 | 2/2007 | Gelfand et al. |
| 7,214,312 B2 | 5/2007 | Brugger et al. |
| 7,226,538 B2 | 6/2007 | Brugger et al. |
| 7,241,272 B2 | 7/2007 | Karoor et al. |
| 7,252,767 B2 | 8/2007 | Bortun et al. |
| 7,267,658 B2 | 9/2007 | Treu et al. |
| 7,273,465 B2 | 9/2007 | Ash |
| 7,276,042 B2 | 10/2007 | Polaschegg et al. |
| 7,300,413 B2 | 11/2007 | Burbank et al. |
| 7,309,323 B2 | 12/2007 | Gura et al. |
| 7,314,208 B1 | 1/2008 | Rightley |
| 7,337,674 B2 | 3/2008 | Burbank et al. |
| 7,338,460 B2 | 3/2008 | Burbank et al. |
| 7,347,849 B2 | 3/2008 | Brugger et al. |
| 7,959,129 B2 * | 6/2011 | Matsumoto ............ 251/129.19 |
| 2002/0068364 A1 | 6/2002 | Arai et al. |
| 2002/0085951 A1 | 7/2002 | Gelfand et al. |
| 2006/0122552 A1 | 6/2006 | O'Mahony |
| 2007/0161113 A1 | 7/2007 | Ash |
| 2008/0041136 A1 | 2/2008 | Kopelman et al. |
| 2008/0264498 A1 * | 10/2008 | Thompson et al. ........... 137/554 |

* cited by examiner

VALVE SYSTEM

FIELD OF THE INVENTION

The present invention generally relates to the field of valves and more specifically to an electrically driven, magnetic valve for use in kidney dialysis systems where low power consumption, low heat generation, high reliability and a small, light size are functional requirements.

BACKGROUND OF THE INVENTION

Valves are widely used to control the flow of fluids through systems. Valve requirements vary dramatically depending upon the nature and scope of the application. In a kidney dialysis system, particularly portable kidney dialysis systems, the functional requirements for a valve include low power consumption, low heat generation, high reliability and a small, light size.

Typically, automated valves in kidney dialysis systems require energy input to maintain at least one state, namely an open state or closed state. However, the on-going need for energy input to maintain a state has substantial disadvantages. First, the system requires a higher amount of energy, thereby decreasing system mobility. Second, a system failure can cause a cut off in energy supply, thereby adversely affecting the state of a valve and causing a major secondary system failure that can hurt a kidney dialysis patient.

Valves that operate between two states (open and closed) in which energy input is required to change a state, but not to maintain a state, are known. For example, U.S. Pat. Nos. 6,836,201, 5,322,258, 6,517,045, and 7,314,208 all of which are incorporated by reference, disclose valves in which energy input is required to change a state, but not to maintain a state. However, these valve systems have not been applied, or were suggested to be applied, to the field of kidney dialysis. Moreover, they are typically not suitable for reliably maintaining the valve's closed state at the size dimensions, reliability, and force levels required by kidney dialysis systems.

In sum, valves disclosed in the medical, and more specifically kidney dialysis, fields of art are not suitable to effectively meet the aforementioned functional needs. Accordingly there is need in the prior art for an improved valve with the aforementioned attributes.

SUMMARY OF THE INVENTION

In one embodiment, the present invention is directed to a valve having an open position and a closed position comprising an orifice closing member adjacent to an orifice through which fluid can flow, a displacement member having a first portion and a second portion, wherein said first portion is adjacent to the orifice closing member when the valve is in said open position, a first magnet and a second magnet wherein said first and second magnets are sufficiently proximate to said displacement member to exert a magnetic force on said displacement member, and an actuator for generating a magnetic field to move said displacement member toward said first magnet, cause said first portion to press against the orifice closing member, and cause the orifice closing member to close said orifice.

Optionally, the first portion comprises a housing, compliant material, such as a spring, a rod and a gap between the compliant material and the rod. The valve further comprises an optical sensor positioned to sense if a gap in said valve is present or absent. The first portion comprises a rod and the second portion of the displacement member is a metal body with a diameter greater than said rod. The rod is bonded to said cylinder. The first magnet is larger than said second magnet. The orifice closing member comprises at least one of a diaphragm, an elastic material, a compliant material and a compressible material. The orifice is part of a manifold for a kidney dialysis system. The orifice closing member compresses against a valve seat to close said orifice. The valve seat is part of a manifold for a kidney dialysis system. The orifice closing member is part of a manifold for a kidney dialysis system.

In another embodiment, the valve comprises a) an orifice closing member adjacent to an orifice through which fluid can flow wherein said orifice closing member compresses against a valve seat when the valve is in a closed position, b) a moveable member that is physically movable relative to said orifice closing member wherein said moveable member moves from a first position when said valve is in an open position to a second position when said valve is in said closed position and wherein, in said second position, the moveable member presses against the orifice closing member to cause said orifice closing member to compress against the valve seat, c) a first magnet and a second magnet having a separation wherein said first magnet and second magnet generate a magnetic field in the separation and wherein said magnetic field has a direction; and d) an actuator capable of generating an electromagnetic force, wherein said electromagnetic force reverses the direction of said magnetic field.

Optionally, the valve further comprises an optical sensor positioned to sense if a gap is present or absent. The moveable member comprises a rod and a cylinder with a diameter greater than the rod, along with a compliant material, such as a spring. The first magnet is larger than the second magnet. The orifice closing member and valve seat are part of a disposable manifold for a kidney dialysis system.

In another embodiment, the valve comprises a) a diaphragm, b) a valve seat adjacent to the diaphragm, wherein, when the valve is in a closed state, said diaphragm compresses against the valve seat and causes a sealing of the orifice through which fluid can flow and wherein, when the valve is in an open state, the diaphragm does not compress against the valve seat, c) a displacement member comprising a rod bonded to a cylinder wherein said displacement member is moveable relative to the diaphragm, wherein the rod does not compress the diaphragm when the valve is in the open position, and wherein the rod compresses the diaphragm when the valve is in the closed position, d) a first magnet and a second magnet wherein the first magnet is larger than the second magnet, wherein the first magnet exerts a greater magnetic force on the cylinder than the second magnet when the valve is in the closed position and wherein the second magnet exerts a greater magnetic force on the cylinder than the first magnet when the valve is in the open position, and e) an actuator for generating the magnetic force exerted by said first magnet on said cylinder.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION OF THE INVENTION

Figure 1:
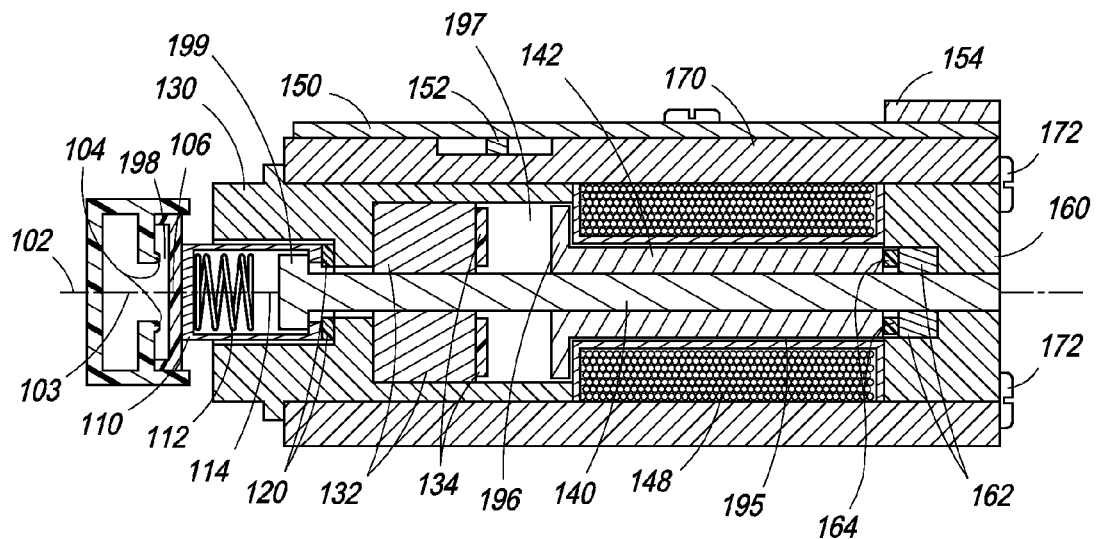
FIG. 1 depicts an embodiment of a valve of the present invention where the valve is in an open state.

While the present invention may be embodied in many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The present invention comprises a system that functions as a fluidic valve in a kidney dialysis system, such as a portable kidney dialysis system. The system comprises a magnetic displacement system that is lightweight and consumes minimum power, making it ideal even when the portable kidney dialysis system uses a disposable manifold for fluidic circuits. The system can be used in conjunction with an orifice in any structure. In particular, an orifice is any hole, opening, void, or partition in any type of material. This includes pathways in tubing, manifolds, disposable manifolds, channels, and other pathways. U.S. patent Ser. Nos. 12/324,924, 12/237,914, and 12/245,397, co-owned by the present applicant, disclose exemplary manifolds with which the present invention can be implemented and are incorporated herein by reference. One of ordinary skill in the art would appreciate that the presently disclosed valve system would be implemented with a disposable manifold by positioning the displacement member and magnets, as further discussed below, external to the manifold at the desired valve location. The actuator is also separate and distinct from the disposable manifold and generally part of the non-disposable portion of the kidney dialysis system.

Functionally, the valve of the present invention has two stable states: open and closed. It operates by using magnetic forces to move a displacement member against a diaphragm and thereby create sufficient force to press the diaphragm against a valve seat and cause the diaphragm to close the orifice. Closing of the orifice shuts off fluid flow. The reverse process, namely the use of magnetic forces to move a displacement member away from the diaphragm and thereby release the diaphragm from compression against the valve seat, opens the orifice and permits fluid to flow.

Figure 2:
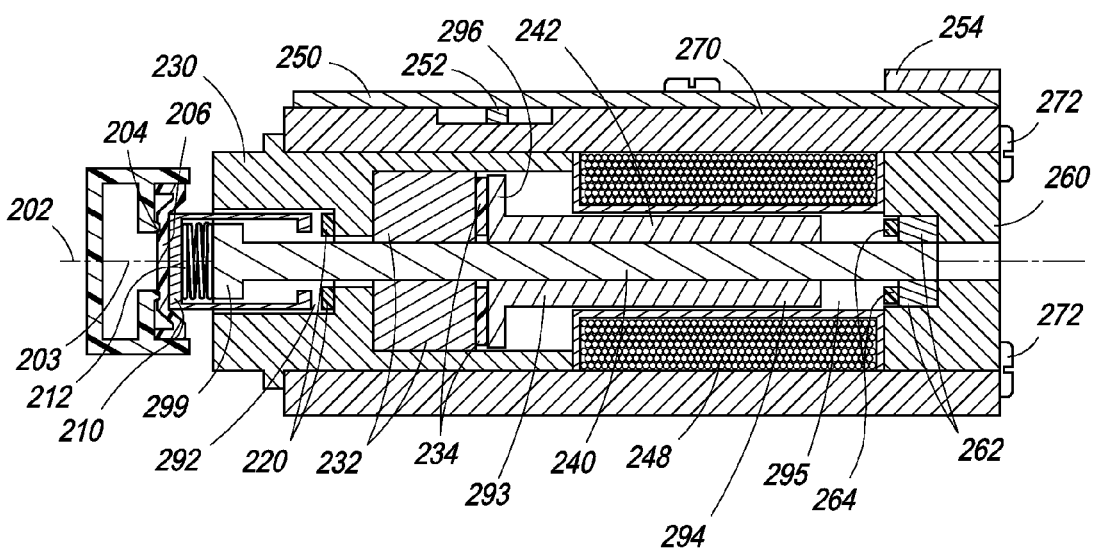
FIG. 2 depicts an embodiment of a valve of the present invention where the valve is in a closed stated.
Figure 4:
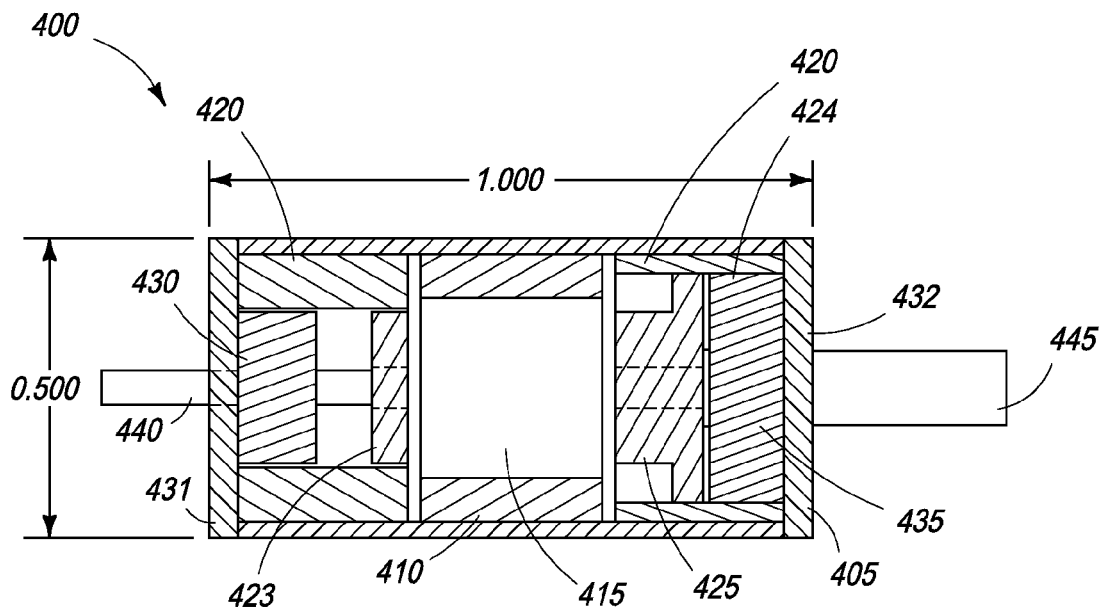
FIG. 4 shows a schematic diagram of another embodiment of a displacement member and mechanism of the present invention.

It should be appreciated that while the present invention shall be discussed in terms of a preferred embodiment, depicted in FIGS. 1 and 2, and a non-preferred embodiment, depicted in FIG. 4, the present invention is generally directed to any use of a valve in a kidney dialysis system having the following attributes: a) two stable states, open and closed, b) changing states requires energy input, c) maintaining a state does not require energy input, d) a state is changed by the use of magnetic forces to modify the position of a displacement member which, when modified, causes a valve to either open or close.

In one embodiment, referring to FIG. 1, the valve system of the present invention 100 is used to control fluid flow through a fluidic flow channel 102, which is bounded by valve seats 104 to thereby create a valve annular orifice 103. As discussed above, orifice 103 is any hole, opening, void, or partition in any type of material, in particular, manifolds, disposable manifolds, channels, and other pathways. The valve 100 is shown in an open state. The components of the valve system include an orifice closing member, a displacement member, a mechanism for moving the displacement member, an optional optical sensor, a coil driver circuit, and an actuator having a coil.

In one embodiment, the orifice closing member comprises a diaphragm 106 which, when compressed by the displacement member, as discussed below, presses against the valve seats 104, thereby causing the valve annular orifice 103, to close. In an open state, the main body of the diaphragm 106 is separated from the valve seats 104 by a gap 198. In one embodiment, the diaphragm 106 is made from a soft material such as silicone rubber. The diaphragm 106 must maintain its shape over time, temperature, and actuations. The valve 100 relies upon the diaphragm material 106 to return to its uncompressed shape when the displacement member (compressing force) is removed, the open state.

One of ordinary skill in the art should appreciate that the orifice closing member can comprise any combination of spring, compressible, or non-compressible structures which, when pushed by the displacement member, closes the orifice. In one embodiment, the valve seats 104 can be molded into a manifold. Suitable materials for the valve seat are polycarbonate, ABS and similar plastics. The valve orifice 103 in the preferred embodiment ranges from 0.1 to 0.3 inches in diameter (and more particularly 0.190 inches). Orifice dimensions can be increased to increase flow for alternate applications of the invention or, alternatively, decreased to decrease flow for alternate applications.

In one embodiment, the displacement member comprises a plunger cap, or housing, 110, which, when the valve is in an open state, is aligned against the diaphragm 106, but not substantially compressing the diaphragm 106. Positioned inside the plunger cap 110 is a compliant component, such as a spring, 112 and the head of plunger 199, which are separated by an air gap 114. The plunger cap 110 is encompassed bound on the outside by a fluid seal 120, which in one embodiment, is a thin, soft silicone rubber washer. In one embodiment, the plunger cap 110 is forced against the silicone rubber washer and compresses the washer to form the fluid seal 120. When in a closed position, the plunger cap 110 is not forced against the washer, which is therefore not compressed and positioned loose to the end cap 130. The spring 112 is any elastic or compliant material and, in one embodiment, comprises a waves spring.

The plunger cap 110, internal spring 112, air gap, plunger head 199, plunger body 140, and core 142 are the components of the preferred displacement member of the present invention. In one embodiment, the plunger body 140 has an outer diameter in the range of 0.1 to 0.2 inches (more particularly 0.122 inches) and is approximately 0.5 to 2.5 inches long. It should be appreciated that the plunger body 140 is any rod structure of any length, depending on the application. The plunger body 140 is positioned within an annular core 142, which has one larger end and one smaller end, and is attached to the core via any method known to ordinary skill in the art, including epoxy, screw attachment, pinned, or welded. The outer diameter of the larger end of the core 142 is in the range of 0.3 inches to 0.5 inches (and more particularly 0.395 inches), the thickness is in the range of 0.03 to 0.15 inches (and more particularly 0.05 to 0.10), and the length is in the range of 0.50 to 1.75 inches long (and more particularly 1.05 inches). The small end of the core 142 has a diameter of 0.1 to 0.4 inches, and more particularly 0.25 inches.

At least partially encompassing the small end of the core is a coil bobbin 195, which keeps the coil 148 in place and provides dimensional stability to the coil 148. A gap preferably exists between the coil bobbin 195 and core 142. The size of the gap is approximately 0.01 to 0.03 inches (and more particularly 0.02 inches). The coil bobbin 195 is, in one embodiment, a glass filled nylon structure, which should be nonmetallic and non-ferromagnetic. The coil bobbin 195 is an annular structure with an outer diameter of a size sufficient to provide a tight fit into the housing bore and an inner diameter sufficient to enclose the core such that it has room to move and undergo some degree of thermal expansion. The two end caps 130, 160 wedge the bobbin 195 into place and keep it from moving or slipping, particularly when exposed to electromagnetic forces.

The plunger body is made of metal or non-metal material, such as brass or fiberglass, and the core is also made of metal, particularly steel 1018 or 1117. Preferably, the plunger body is non-magnetic and the core body is ferrous-magnetic. As discussed further below, the plunger body 140 and core 142 are moved by the mechanism for moving the displacement member, as further described below.

The mechanism for moving the displacement member comprises a large magnet component, a small magnet component and a housing within which the magnets and a portion of the displacement member, namely the plunger body 140 and core 142, are contained. More particularly, referring to FIG. 1, the mechanism to moving the displacement member comprises a large magnet end cap, to hold and align the large magnet, 130, a large magnet 132, an elastic material 134, a gap 197, a coil 148, a small magnet component 162, a small magnet mount and end cap 160, and an elastic material 164.

The large magnet end cap 130 holds and aligns the large magnet component 132 and coil bobbin 195 in place within a housing 170, referred to as the actuator body which has a borehole through which the components described herein are placed. The large magnet component 132 needs to be properly aligned with the core 142, plunger body 140, and small magnetic component 162 to ensure the proper movement of the displacement member. Both end caps 130 and 160 secure the coil bobbin 195 and coil 148 in position. Additionally, a mounting plate can be used to capture and hold end cap 130. In one embodiment, the mounting plate is positioned vertically and flush against the side of the end cap and between the end cap and bore. The mounting plate has a hole in it, roughly same size as the smaller diameter of the end cap. A clamping mechanism holds the body against the plate; alternatively the plate can be permanently fixed, using any boding technique known to persons of ordinary skill in the art. Unlike the prior art, such as U.S. Pat. No. 6,836,201, in a preferred embodiment, the magnets are located inside, not outside, the bore and provide bearings for the plunger, as discussed below.

The large magnet component 132 is separated from the core 142 by a gap 197 and elastic material 134, such as a silicone washer, which, in one embodiment, has an outer diameter of 0.3 to 0.5 inches (and more particularly 0.37 inches), an inner diameter of 0.1 to 0.3 inches (and more particularly 0.188 inches), a thickness of 0.005 to 0.015 inches (and more particularly 0.01 inches), and a durometer of 35 to 45 (and more particularly 40). The small magnet component 162 is separated from the core by an elastic material 164, such as a silicone washer, which, in one embodiment, has an outer diameter of 0.1 to 0.4 inches (and more particularly 0.24 inches), an inner diameter of 0.1 to 0.3 inches (and more particularly 0.188 inches), a thickness of 0.005 to 0.015 inches (and more particularly 0.01 inches), and a durometer of 35 to 45 (and more particularly 40). The small magnetic component 162 is held and kept properly aligned within the housing 170 by a small magnet mount and end cap 160. The small magnet end cap screws 172 also serve to capture and hold in place the small magnet end caps 160.

Referring to FIG. 1, the valve system of the present invention further comprises a coil driver circuit board 150, which drives the actuator, comprising coil 148, and is preferably mounted to the actuator body 170 via small screws, a coil driver connector 154, and an optical sensor 152, which senses the position of the large end of the core 196. Coil 148 serves to effectuate changes in magnetic fields in order to cause movement of the core 142 and plunger body 140. In one embodiment, the coil is approximately 0.05 to 1.5 inches long (and more particularly 1 inch long), has an outer diameter of 0.35 to 0.55 inches (and more particularly 0.46 inches), and an inner diameter of 0.15 to 0.35 inches (and more particularly 0.26 inches), with six layers of wire 29 AWG wire. The various elastic materials used in the displacement member and mechanism for moving the displacement member to provide a "soft" stop to the movement of the rod 140 when the valve opens or closes. In particular, it serves to ensure the movement of the core does not damage the magnets.

The large magnet component 132 can be one unitary magnet or, in a preferred embodiment, comprised of a plurality of magnets, such as three. The small magnet component 162 can also be unitary or comprised of a plurality of magnets. In one embodiment, the magnets are made of is preferably Alnico, Samarium Cobalt, Neodymium, Rare Earth, or Ceramic magnets. In one embodiment, the large magnet 132 is a Neodymium ring magnet with an outer diameter of 0.2 to 0.5 inches (and more particularly 0.375 inches), an inner diameter of 0.05 to 0.3 inches (and more particularly 0.125 inches), and a length of 0.2 to 0.5 inches (and more particularly 0.375 inches). In one embodiment, the small magnet 162 is made of Neodymium ring magnet, with an outer diameter of 0.15 to 0.4 inches (and more particularly 0.25 inches), an inner diameter of 0.05 to 0.3 inches (and more particularly 0.125 inches), and a length of 0.15 to 0.4 inches (and more particularly 0.25 inches). The larger magnet 132 is used closer to the orifice closing member because the size is necessary to generate sufficient opposition force to the valve seat. Further, the actuation force caused by the actuation coil is substantial equal even though the magnets are different size, thereby enabling a simple coil driver circuit.

In one embodiment, the rod, plunger or other elongated member 140 uses the magnets' center holes as a linear bearing. Accordingly, the magnets' center holes should preferably have a bearing surface, such as chrome or any smooth hard surface with minimal friction. A gap is placed between the coil bobbin 195 and the core 142 because of thermal expansion of the bobbin, bobbin creepage over time, and bobbin, core, and magnets tolerances. However, under all operating conditions, the gap should be sufficient such that the plunger body 140 can move freely and not bind in the openings of the magnets and coil. In a preferred embodiment, the gap is approximately 0.01 to 0.06 inches (and more particularly 0.02 inches) at room temperature.

When the valve is closed, referring to FIG. 2, the valve system of the present invention 200 controls fluid flow through a fluidic flow channel 202, which is bounded by valve seats 204, by compressing the orifice closing member, e.g. diaphragm 206, and thereby obstruct valve annular orifice 203. In a closed state, the main body of the diaphragm 206 is pressed against the valve seats 204 and, accordingly, substantially eliminates gap 198 (seen in FIG. 1).

Once just adjacent to the diaphragm 206, the displacement member now compresses the diaphragm 206. In particularly, plunger cap 210 has moved to compress the diaphragm 206. The plunger cap 210 has moved because a change in magnetic fields causes the core body 242 to move toward the large magnet component 232. The core body 242 stops moving when the core head 296 passes through the gap 197 (in FIG. 1) and stops at the elastic material 234 positioned adjacent to the large magnet component 232. Movement of the core 242 causes the plunger body 240, to which the core 242 is bonded, to move as well. Movement of the plunger body 240 causes the plunger head 299 to move within the plunger cap 210, pass through the gap 114 (in FIG. 1), and compress the spring 212. After a certain amount of compression, the plunger cap 210 moves and compresses the diaphragm 206. Movement of the plunger cap 210 creates a new gap 292 between the cap body 210 and the elastic material 220 that is positioned adjacent to the large magnet end cap 230.

As shown in FIG. 2, the other components of the valve remain the same, including the actuator body 270, coil driver circuit 250, coil connector 254, coil 248, coil bobbin 293, small end cap screws 272, optical sensor 252, small magnet end cap 260. It should be appreciated however, that, by virtue of the core 242 movement, a gap 295 is created between the smaller end of the core 294 and the elastic material 264, which is positioned adjacent to the small magnetic component 262.

It should be appreciated that, to close the valve, the displacement member applies a force to the orifice closing member, e.g. diaphragm 206. The force required, from the displacement member, to deform the diaphragm to the point where the diaphragm touches the valve seat is substantially linear and can be modeled as a linear spring. However, the force requirements increase exponentially as the diaphragm is compressed into the valve seat. Thus, the force profile for the displacement member becomes nonlinear and far more complex. Accordingly, there are several unique challenges associated with the design of the valve and the tolerances between the various components of the displacement member, the orifice closing member, and the hard stop of the displacement mechanism. The displacement mechanism must be able to deliver the nonlinear force profile without permanently deforming the diaphragm. This means that the mechanism must deliver just the right amount of force.

As discussed above, the displacement member comprises a rod, plunger or other elongated member that is bonded to another structure, referred to as a core, which has a larger diameter and can function as a stopper when forced up against another structure, such as a magnet face. One of ordinary skill in the art should appreciate that the displacement member or moveable member is not limited to a rod and cylinder configuration. On the contrary, it can include non-cylindrical structures, unitary pieces, or multiple pieces that are welded or, in any other manner, bonded together. In sum, the displacement member can comprise many different structures, provided the movement of the member can exert the requisite force on the orifice compressing member in a manner that is reliable and consistent.

For example, referring to FIG. 4, an alternate, less preferred embodiment is shown. For kidney dialysis applications, this embodiment does not typically reliably maintain the valve in a closed state. The displacement member 400 comprises a housing 405 that includes an electromagnet 410 with a substantially cylindrical structure and a borehole 415 running through it. The electromagnet 410 is securely positioned centrally within the housing 405 by non-magnetic spacers 420 which, in one embodiment are the end caps. The end caps have two purposes—hold the magnets in place and sandwich the coil in place. In one embodiment, elements 431 and 420 comprise a first unitary piece and 405 and 420 comprise a second unitary piece. A cylindrically shaped ferromagnetic core 425, having a first face 423 and a second face 424, is positioned to allow a portion of the core 425, between the first face 423 and the second face 424, to have a linearly slide-able fit with the bore 415. The second face 424 is sufficiently larger than the bore 415 thereby restricting the linear motion of the core 425. In one embodiment, the second face is differently sized relative to the first face to generate sufficient magnetic to keep the valve in a closed position. The core 425 is capable of left and right linear sliding motion within the bore 415.

Two differently sized magnets 430, 435 are also affixed within and at the two end caps 431, 432 of the housing 405. The first face 423 of the core 425 contacts with the first magnet 430 to form a first stable state of the displacement system 400 and the second face 424 of the core 425 contacts with the larger magnet 435 to form a second stable state of the displacement system 400. The placement of the permanent magnets 430, 435 is designed to be within the diameter of housing 405, as it reduces the size of the displacement system 400. A first rod 440 connected to the first face 423 of the core 425 passes through the first magnet 430 thereby protruding from the housing 405 at one end and a second rod 445 connected to the second face 424 of the core 425 passes through the second magnet 435 thereby protruding from the housing 405 at the other end. The rods 440, 445 can be made of non-corrosive, non magnetic, material known in the art, such as but not limited to, brass. While one embodiment has two rods connected to two faces of the core, in an alternate embodiment there is only one rod connected to one of the faces of the shuttle.

Persons of ordinary skill in the art would appreciate that the magnetic force exerted by the electromagnet 410 on the core 425 is sufficiently high to overcome the retention force of the permanent magnets 430, 435 so that the displacement system 400 can be changed from the first stable state to the second. Moreover, one of ordinary skill in the art would appreciate that the rod/plunger 445 moves with the core 425, thereby creating the motive force to compress or decompress the orifice closing member. However, this embodiment has been determined to be inferior to the first embodiment because it fails to sufficiently hold the closed state.

Several design features of the orifice closing member operating in conjunction with the displacement member and mechanism should be appreciated. First, referring to FIG. 5, and as discussed above in relation to FIGS. 1 and 2, a gap exists between the plunger cap 504 and the orifice closing member 505, in particular the first diaphragm face 505. The gap is in the range of 0.040 to 0.070 inches and more particularly approximately 0.055 inches. The diaphragm comprises silicone, preferably a thickness of 0.040 inches, and can be modeled as a spring ($K_{V2}$) having a spring constant of 270 lbf/in. The second diaphragm face 506 is separated from the valve seat 507 and acted upon by magnetic forces modeled as a spring, $K_{V1}$ having a spring constant of approximately 22.5 lbf/in and a thickness of approximately 0.047 inches.

The rod 504 translates the force generated by the magnetic attraction of the core 501 to the magnet 503 modeled by spring Kp, which is separated from the core head 501 by a washer, e.g. 0.010 inches of silicone in a closed state and is separated from core head 501 by approximately 0.110 inches in an open state. This silicone washer provides forces which are modeled as a spring, $K_{SL}$. The core 501 is bonded to the rod 504. When the valve is actuated, the rod 504 moves in the direction of the valve seat 507 because the core, to which the rod is bonded, moves in the direction of the large magnet 503.

Figure 5:
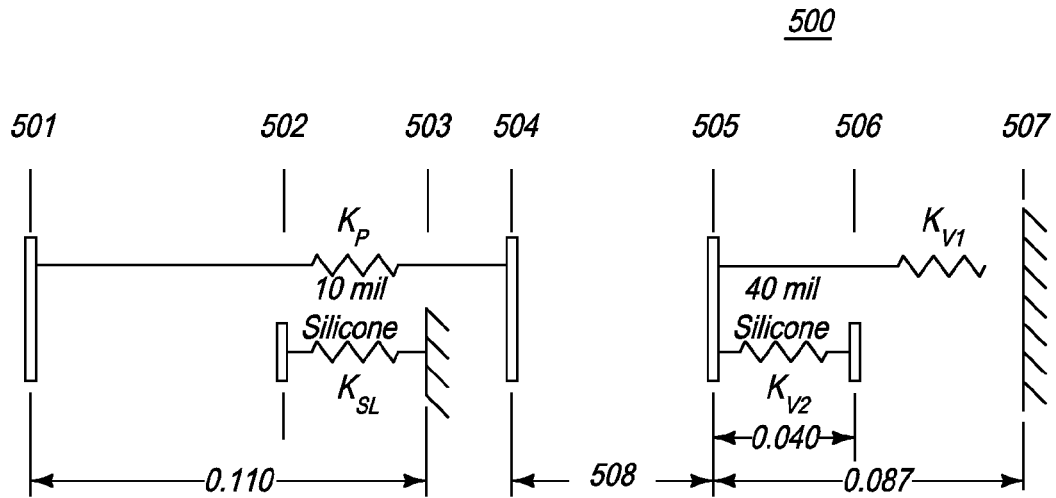
FIG. 5 is a schematic illustration of one embodiment of the displacement system of the present invention when the valve is in an open state.

Referring to FIG. 5, $K_{v2}$ and $K_{SL}$ correspond to elastic material, such as silicone, which are modeled as rigid springs. It should be appreciated that, when a valve is in a closed state, there are two positions of importance. First, is the position of the rod against the diaphragm and the second is the position of the core face against the large magnet. When the valve is closed, the rod is pressing on the valve diaphragm with enough force to resist at least 600 mmHg back pressure generated within the fluid passage of the kidney dialysis system. In this embodiment, fluid pressures can reach 2600 mmHg and this system is designed to maintain the diaphragm firmly pressed against the valve seat to seal the orifice up to and including 2600 mmHg.

Additionally, when the valve is closed, the core's large face is pulled close to, or directly against, the large magnet. The magnetic attraction of the core to the large magnet generates the force that the rod applies to the orifice closing member, e.g. diaphragm. To generate a consistent and reliable force, the spacing between the core face and the face of the large magnet must be consistent. Therefore, it is preferred to place an elastic material 502, 503 between the core face 501 and the magnet face 504. The elastic material has a nonlinear spring constant and will compress until the resultant forces for the elastic material equals the magnetic forces. When the rod applies force to the diaphragm via the core, the core will experience the resultant force. For a static condition to occur, the sum of these forces on the core must equal zero. Furthermore, the elastic material serves to protect the magnet face from chipping or breakage during actuation.

Figure 7:
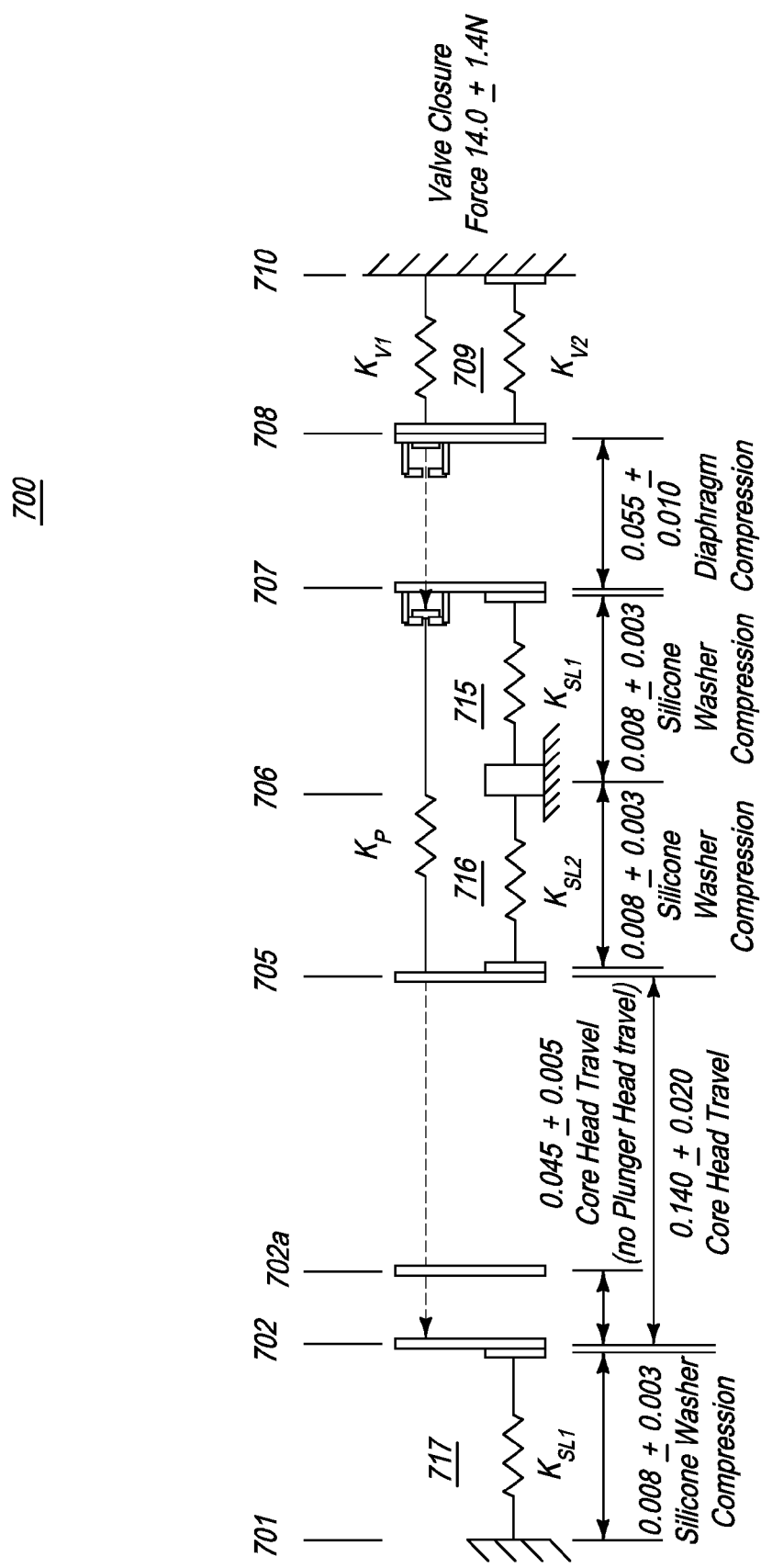
FIG. 7 is a schematic illustration of one embodiment of the displacement system of the present invention when the valve is in a closed state.

Referring to FIG. 7, when the valve 700 is in a closed state, the core head 705, 702 has moved away from the small magnet face 701 (from position 702a to position 702). When in position 702, the core head is separated from the small magnet 701 by an elastic material 717, such as a silicone washer having a thickness of approximately 0.015 inches. When in position 705, the core head will have moved approximately 0.140+/−0.20 inches, including a distance of 0.45+/−0.005 inches during which the rod 708 does not move, and stopped against an elastic material 716 (e.g. a silicone washer having a thickness of approximately 0.015 inches), which separates the core head 705 from the large magnet face 706. The large magnet 706 is, in turn separated from the rod head 707.

When the valve is in an open state, the large magnet 706 is separated from the rod head 707 by an elastic material 715, such as a silicone washer having a thickness of approximately 0.015 inches. When the valve is in a closed state, the large magnet 706 is separated from the rod head 707 by an elastic material 715, such as a silicone washer having a thickness of approximately 0.015 inches and a distance of approximately 0.055+/−0.10 inches. When the valve is closed, the rod head 707 has moved from being proximate to the large magnet 706 and elastic material 715 to being proximate to the valve seat 710. Specifically, the rod head 707 moves to compress the diaphragm 708 and thereby press against an elastic material 709 (e.g. silicone having a thickness of approximately 0.040 inches) which, in turn, presses against the valve seat 710. This causes the valve to close with an approximate force of 14 N.

Figure 6:
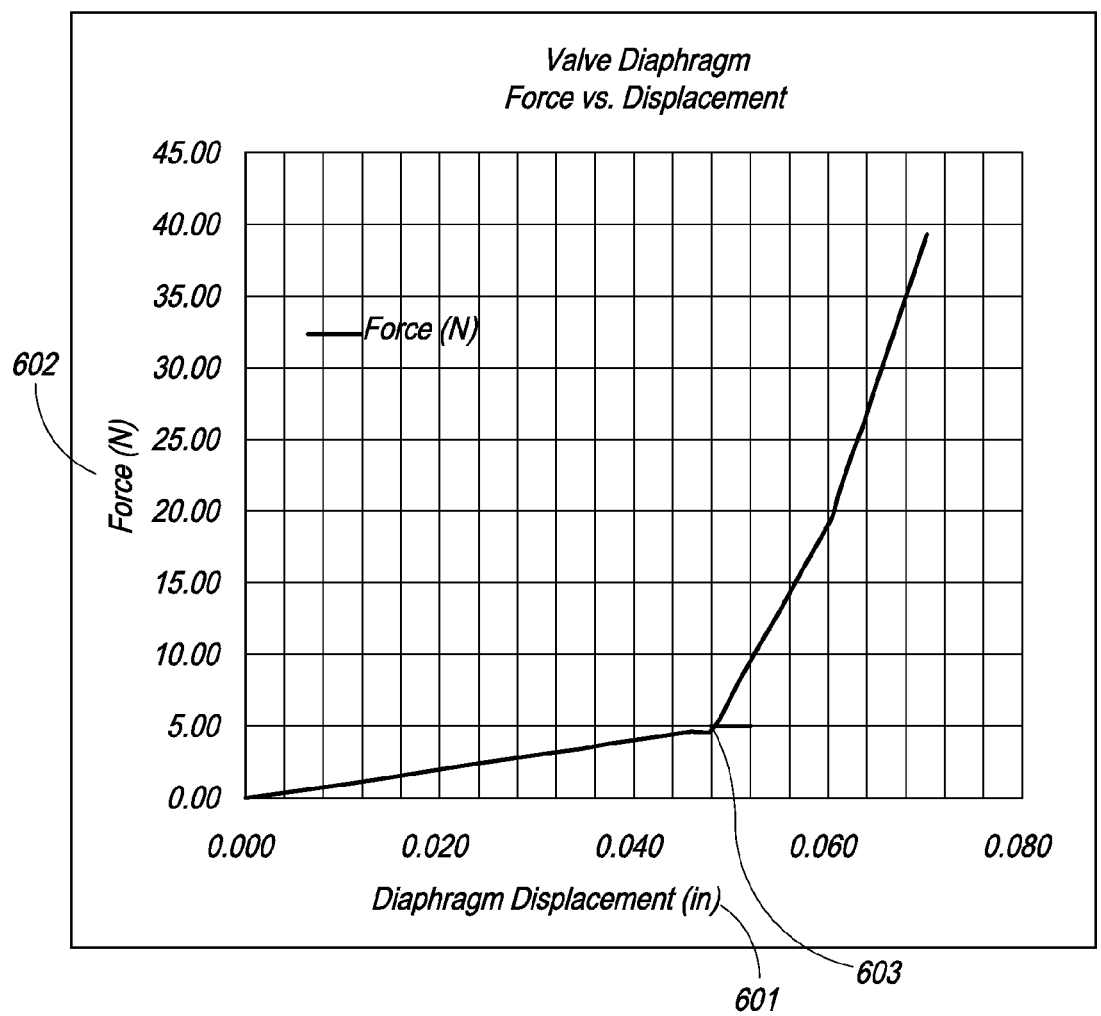
FIG. 6 is a chart showing an exemplary relationship between the force on one embodiment of an orifice compressing member and its displacement.

It should be appreciated that the configuration of the displacement member and mechanism relative to the orifice closing member and the tolerances described herein provide for a diaphragm displacement profile 600, as shown in FIG. 6 which is suitable for applications that need to resist at least 600 mmHg back pressure, such as kidney dialysis systems. Referring to FIG. 6, an exemplary diaphragm displacement profile is provided, where the force 602 exerted by the displacement member is provided on the y-axis and the corresponding diaphragm displacement is provided on the x-axis. The inflection point on this curve 603 indicates when the diaphragm starts being compressed against the valve seat. To the left of the inflection 603, the diaphragm is being forced to flex toward the valve seat, but there is no substantial compression against the valve seat. To the right of the inflection point 603, the diaphragm is flexed against the valve seat, deforming the diaphragm material and affecting a good seal against the fluid pressure.

Figure 3:
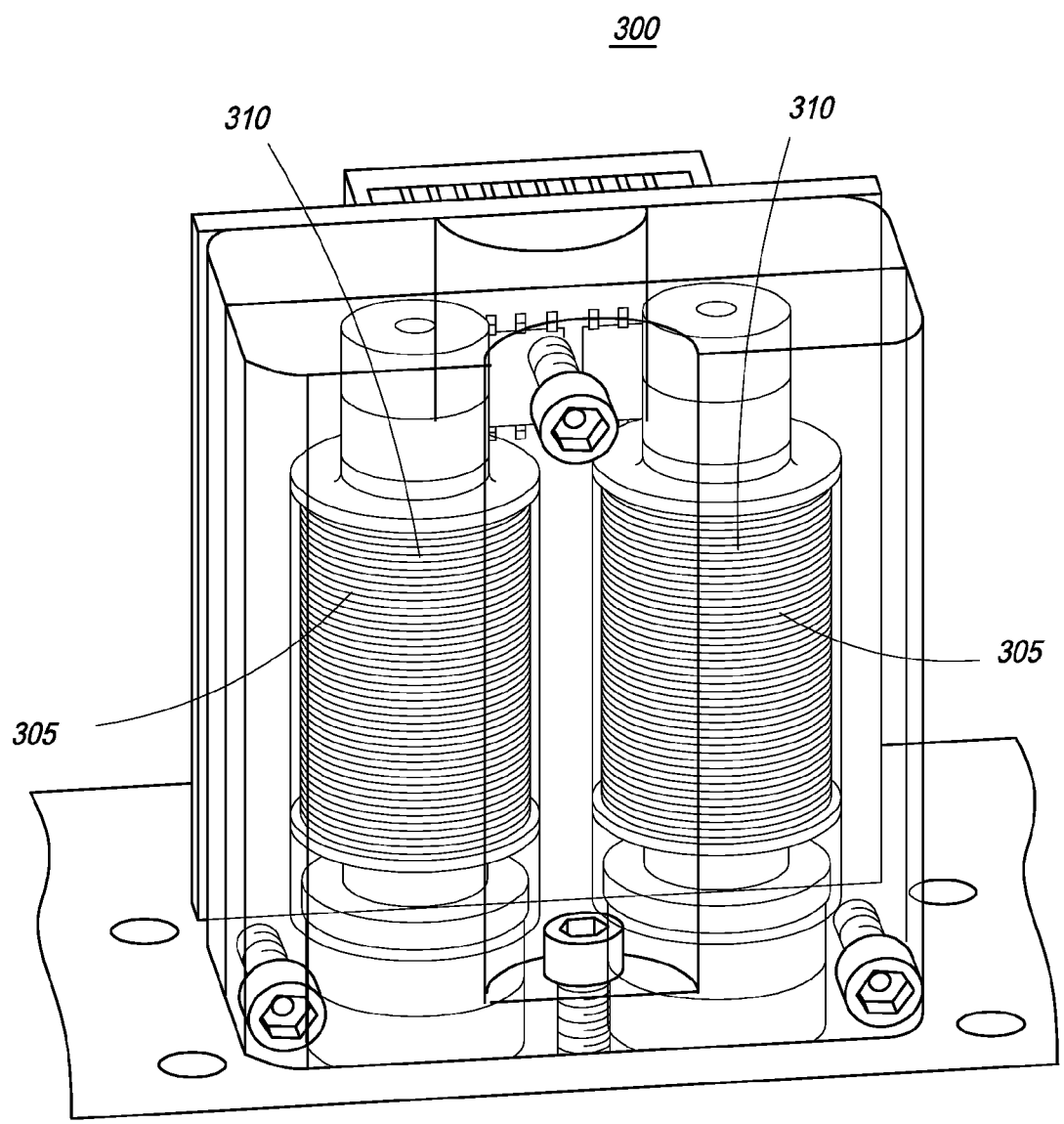
FIG. 3 is a diagram of one embodiment of the actuator.

Another important component of the displacement mechanism system is an actuator system 300. Referring to FIG. 3, during the actuation process, coils 305 are energized and the magnetic field builds, thus creating magnetic force opposing the small magnet attraction force. As the force builds, the core, discussed above, starts to move to the close position (large magnet). Once the core moves past a point of no return, the attraction forces on the core of the large magnet has overcome the attraction forces of the small magnet. To ensure that the opposing forces caused by the valve diaphragm do not overcome the attraction force of the large magnet, a gap is provided, as discussed above.

The coil design is made of coil form and magnet wire. The size of the coil form size is preferably based upon commercially available coil forms the pulsed current capability of the power supply, and, in particular, the required actuation force and the power supply voltage. The actuation force is proportional to the amp-turn rating of the coil. In one embodiment, it is preferred to limit the coil current to 6 amperes or less.

Factors important in the coil design include the number of layers, packing factor, wire diameter, and coil resistance. In one embodiment, the present invention uses a bobbin 310 with 6 layers of wire 305 and approximately 0.010 inches space between the bobbin flange diameter and the last layer. With an insulation requirement of heavy poly nylon and a coil resistance of 3.5+/−0.5 Ohms, the wire size 305 is approximately 29 AWG. Any size coil form can be used.

The circuit used to drive the coil is an H-bridge circuit which enables current to be reversed for open and closed operations. The H-Bridge circuit is driven via a unique pulse width modulated (PWM) signal. The PWM signal is used to generate a cosine current pulse through the coil. The period of the cosine pulse is related to the mass of the core and the opposing force. The preferred embodiment does not use a bipolar DC power switch or sense switch; rather, the optical sensor operates to determine the position of the core, conclude the valve state, and generate an electronic drive cosine waveform to move the plunger in the desired direction, thereby changing the state of the valve.

Optionally, as shown in FIGS. 1 and 2 as elements 152, 252, the valve system uses a sensor, preferably an optical sensor, to determine the state of the valve (open or closed). This can be achieved by positioning the optical sensor in a location that has a sufficient difference in reflectivity, or other optical properties, between a valve open state and a valve closed state. For example, when the valve is closed, in one embodiment, the large end of the core 296 is positioned against an elastic material 234 and the large magnet component 232. The large end of the core 296 has a width wide enough to be sensed by a reflective optical sensor, but not too wide so the optical sensor has position resolution. The optical sensor will be placed on the outside of the displacement member/mechanism and look through its body, which is preferably made of transparent polycarbonate. The optical sensor's wavelength will be in the near infrared range (NIR) so as to have good transmission through the polycarbonate body. One of ordinary skill in the art would appreciate that the sensor can be chosen to suit any material structure, provided it includes the appropriate filters. Here, the optical sensor preferably has built into it a long pass optical filter for NIR responsivity.

Functionally, when the core is in the open position, as shown in FIG. 1, the large end of the core 196 moves out of the field of view of the optical sensor 152, thus very little reflection will be seen by the optical sensor. When the large end of the core 296 is in the field of view, as shown in FIG. 2, there will be a reflection that the sensor will see, thus indicating the core is in the closed position. One of ordinary skill in the art would appreciate that the sensor can be positioned such that it senses a great deal of reflectivity from the core when the valve is in the open position and much less reflectivity (because the core is moved out of the field of view) when the valve is in the closed position. Further, one of ordinary skill in the art would appreciate that the sensor could be positioned proximate to the gap to sense when the gap is present and when the gap is absent, thereby indicating the state of the valve.

Figure 8:
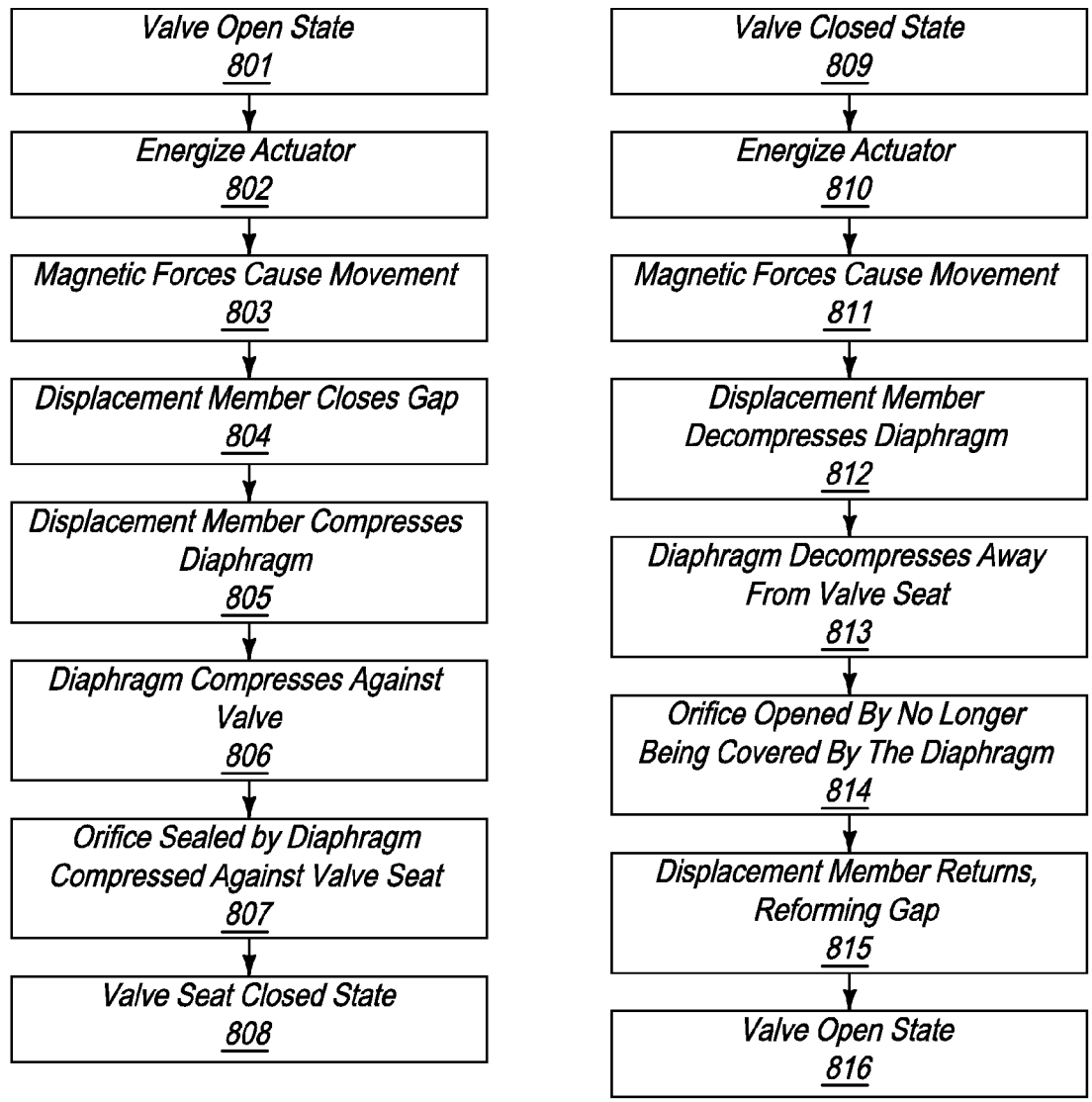
FIG. 8 is a flowchart describing steps for how the valve opens and closes.

Operationally, as referred to in FIG. 8, a valve is initially one of two states, open or closed. Assuming the valve is in an open state 801, the first step in closing the valve is to energize the coil driver circuit 802 and thereby cause the magnetic field generated by the coil to pass through the core, create an opposing magnetic force between the core and small magnet, and create a weak attraction force between the large magnet and the large end of the core. As the displacement member starts to move 803, the small magnet attraction force diminishes as the large magnet attraction forces increases. The displacement member moves 803 until a point of no return, after which the displacement member 804 closes a gap 804 and compresses the orifice closing member, namely the diaphragm 805, against the valve seat 806. The compression of the diaphragm 806 causes the diaphragm to close the orifice 807 and close the valve 808.

Referring to FIG. 8, assuming the valve is in a closed state 809, the first step in opening the valve is to energize the coil driver circuit 810 and thereby cause the magnetic field generated by the coil to pass through the core, create an opposing magnetic force between the core and large magnet, and create a weak attraction force between the small magnet and the small end of the core. As the displacement member starts to move 811, the large magnet attraction force diminishes as the small magnet attraction forces increases. The displacement member moves 811 until a point of no return, after which the displacement member decompresses the diaphragm 812 away from the valve seat 813. The orifice opens by virtue of no longer being covered by the diaphragm 814. The displacement member returns to its original position and recreate the gap 815.

Since the first and second stable states of the core are maintained even when power to the electromagnet is switched off, this allows for the displacement system to have low power consumption and low heat generation relative to prior art actuators where continuous power supply is needed to maintain states, additionally resulting in high heat generation.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

I claim:

1. A valve having an open position and a closed position comprising:
    a. an orifice closing member adjacent to an orifice through which fluid can flow;
    b. a displacement member having a first portion and a second portion, wherein said first portion is adjacent to the orifice closing member when the valve is in said open position and wherein the first portion comprises a housing, elastic material, a rod and a gap between said elastic material and said rod;
    c. a first magnet and a second magnet wherein said first and second magnets are sufficiently proximate to said displacement member to exert a magnetic force on said displacement member; and
    d. an actuator for generating a magnetic field to move said displacement member toward said first magnet, cause said first portion to press against the orifice closing member, and cause the orifice closing member to close said orifice.

2. The valve of claim 1 further comprising an optical sensor positioned to sense if a gap in said valve is present or absent.

3. A valve having an open position and a closed osition comprising:
    a. an orifice closing member adjacent to an orifice through which fluid can flow;
    b. a displacement member having a first portion and a second portion, wherein said first portion is adjacent to the orifice closing member when the valve is in said open position and wherein the first portion comprises a rod bonded to a cylinder and said second portion of said displacement member is a metal body with a diameter greater than said rod;
    c. a first magnet and a second magnet wherein said first and second magnets are sufficiently proximate to said displacement member to exert a magnetic force on said displacement member; and
    d. an actuator for generating a magnetic field to move said displacement member toward said first magnet, cause said first portion to press against the orifice closing member, and cause the orifice closing member to close said orifice.

4. The valve of claim 1 wherein said first magnet is larger than said second magnet.

5. The valve of claim 1 wherein the orifice closing member comprises at least one of a diaphragm, an elastic material, and a compressible material.

6. The valve of claim 1 wherein the orifice is part of a manifold for a kidney dialysis system.

7. The valve of claim 1 wherein the orifice closing member compresses against a valve seat to close said orifice.

8. The valve of claim 7 wherein the valve seat is part of a manifold for a kidney dialysis system.

9. The valve of claim 7 wherein the orifice closing member is part of a manifold for a kidney dialysis system.

* * * * *